United States Patent
Yazawa et al.

(10) Patent No.: US 9,612,220 B2
(45) Date of Patent: Apr. 4, 2017

(54) HUMIDITY SENSING APPARATUS

(71) Applicant: ALPS ELECTRIC CO., LTD., Tokyo (JP)

(72) Inventors: Hisayuki Yazawa, Niigata-ken (JP); Shuji Yanagi, Niigata-ken (JP); Atsushi Tondokoro, Niigata-ken (JP); Hisanobu Okawa, Niigata-ken (JP)

(73) Assignee: ALPS ELECTRIC CO., LTD., Tokyo (JP)

( * ) Notice: Subject to any disclaimer, the term of this patent is extended or adjusted under 35 U.S.C. 154(b) by 71 days.

(21) Appl. No.: 14/663,283

(22) Filed: Mar. 19, 2015

(65) Prior Publication Data
US 2015/0355124 A1 Dec. 10, 2015

(30) Foreign Application Priority Data

Jun. 10, 2014 (JP) .................................. 2014-119473

(51) Int. Cl.
*G01N 27/22* (2006.01)
(52) U.S. Cl.
CPC ................................. *G01N 27/223* (2013.01)
(58) Field of Classification Search
CPC .................................................... G01N 27/223
USPC ...................................................... 73/335.04
See application file for complete search history.

(56) References Cited

U.S. PATENT DOCUMENTS

| | | | | |
|---|---|---|---|---|
| 4,500,940 A * | 2/1985 | Kuisma | ................ | G01N 27/225 361/286 |
| 4,975,249 A * | 12/1990 | Elliott | .................... | G01N 21/81 252/963 |
| 6,690,569 B1 * | 2/2004 | Mayer | .................. | G01N 27/225 361/281 |
| 2005/0188764 A1 * | 9/2005 | Itakura | ................. | G01N 27/223 73/335.04 |
| 2007/0068779 A1 * | 3/2007 | Baldo | ..................... | G01L 5/223 200/16 R |
| 2012/0049885 A1 * | 3/2012 | Monda | ................. | G01R 31/043 324/763.01 |
| 2015/0008593 A1 * | 1/2015 | Takemoto | ........... | H01L 25/0657 257/777 |

FOREIGN PATENT DOCUMENTS

| | | | |
|---|---|---|---|
| JP | 2000-243862 | | 9/2000 |
| JP | 2000243862 A | * | 9/2000 |
| JP | 2002-365256 | | 12/2002 |
| JP | 2008-070200 | | 3/2008 |
| JP | 2008070200 A | * | 3/2008 |

* cited by examiner

*Primary Examiner* — Hezron E Williams
*Assistant Examiner* — Marrit Eyassu
(74) *Attorney, Agent, or Firm* — Beyer Law Group LLP

(57) ABSTRACT

A humidity sensing portion is mounted in a gap between a first opposite member and a second opposite member. Metal joints and dummy joints are provided in the gap between the first opposite member and the second opposite member, and the two opposite members are fixed to each other through the metal joints and the dummy joints. Since only the metal joints and the dummy joints are present in the gap between the two opposite members, gas to be measured is easily introduced into the humidity sensing portion, and the sensing response to the humidity change is improved.

8 Claims, 13 Drawing Sheets

[No. 1]

FIG. 5B [No. 2]
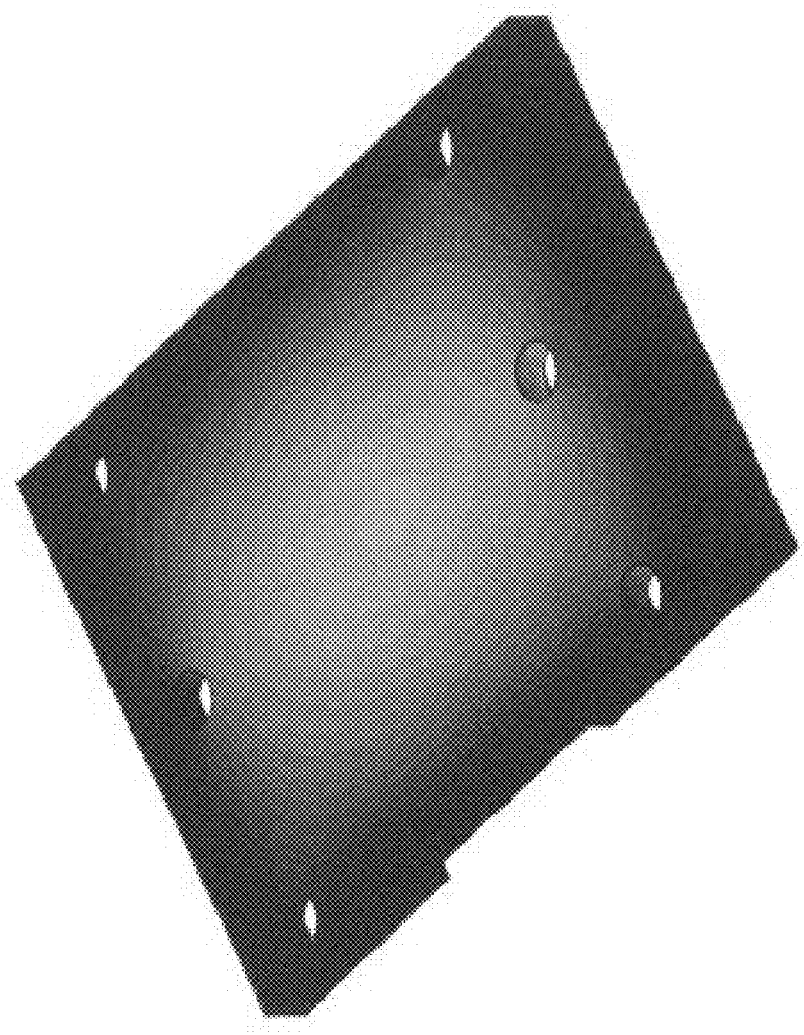
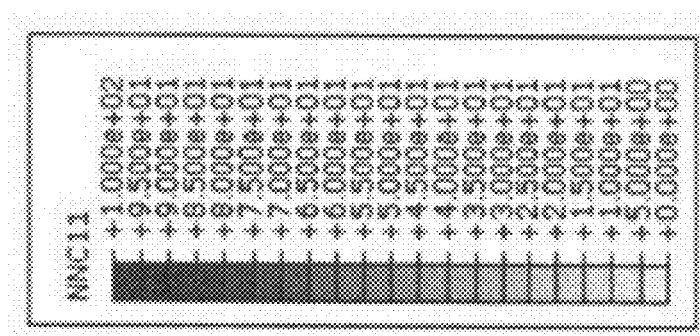

[No. 3]

[No. 4]

[No. 5]

[No. 6]

[No. 7]

HUMIDITY SENSING APPARATUS

CLAIM OF PRIORITY

This application claims benefit of Japanese Patent Application No. 2014-119473 filed on Jun. 10, 2014, which is hereby incorporated by reference.

BACKGROUND OF THE INVENTION

1. Field of the Invention

The present invention relates to a humidity sensing apparatus having a structure capable of reducing the size thereof in which a humidity sensing portion is disposed in a gap between two opposite members.

2. Description of the Related Art

In a humidity sensing apparatus of the related art, a humidity sensing portion and an integrated circuit package, which is equipped with a sensing circuit and the like, are disposed in parallel on a substrate and are coated with a resin material. Since it is necessary to bring the humidity sensing portion into contact with gas to be measured, a measurement hole connected to the humidity sensing portion is formed on a surface of the humidity sensing apparatus.

In the structure of the humidity sensing apparatus of the related art in which the measurement hole connected to the humidity sensing portion is formed toward the outside, when dust or the like infiltrates into the measurement hole, it is difficult to accurately sense the humidity of gas. In addition, in the structure where the humidity sensing portion and the integrated circuit package are disposed in parallel on the substrate, the planar shape of the humidity sensing apparatus increases, and it is difficult to reduce the size thereof.

Japanese Unexamined Patent Application Publication No. 2008-70200 discloses a humidity sensing apparatus including: a substrate; and a sensor chip that forms a humidity sensor and is disposed on the substrate, in which the sensor chip is disposed to be opposite to the substrate with a gap interposed therebetween in a state where a moisture sensitive film faces the substrate. A land provided on the substrate is opposite to an electrode pad provided on the sensor chip, and the land and the electrode pad are joined to each other through a bump electrode so as to be electrically connected.

In addition, a region around the bump electrode is filled with an underfill formed of a resin material having moisture resistance, and the substrate and the sensor chip are fixed to each other through this underfill.

FIG. 9 of Japanese Unexamined Patent Application Publication No. 2008-70200 shows a structure in which a cavity portion with both sides surrounded by the underfill is formed between the substrate and the sensor chip, and a moisture sensitive film is connected to the outside through the cavity portion.

In the humidity sensing apparatus disclosed in Japanese Unexamined Patent Application Publication No. 2008-70200, in order to fix the substrate and the sensor chip opposite to each other, the underfill is filled thereinto in addition to the bump electrode. Therefore, the structure for fixing the substrate and the sensor chip and the fixing work thereof are complicated.

In addition, in the structure shown in FIG. 9 of Japanese Unexamined Patent Application Publication No. 2008-70200, gas is introduced into the moisture sensitive film through the small cavity portion with both sides surrounded by the underfill in a gap between the substrate and the sensor chip. Therefore, when the humidity is changed, a time difference is likely to be generated before the change affects the moisture sensitive film, and the humidity sensing response is decreased.

SUMMARY OF THE INVENTION

The present invention provides a humidity sensing apparatus having a structure including: opposite members; and a humidity sensing portion provided in a gap between the opposite members, in which the opposite members can be joined to each other with a sufficient strength, and gas permeability to the humidity sensing portion is improved to enhance humidity sensing response.

According to an aspect of the present invention, there is provided a humidity sensing apparatus including: a first opposite member; a second opposite member; and a humidity sensing portion, in which an opposite surface of the first opposite member and an opposite surface of the second opposite member are opposite to each other with a gap interposed therebetween, the humidity sensing portion is provided on the opposite surface of the second opposite member, a plurality of electrode portions and a plurality of dummy electrode portions are provided on each of the opposite surfaces, the electrode portions opposite to each other with the gap interposed therebetween are joined to each other through conductive metal joints, and the dummy electrode portions opposite to each other with the gap interposed therebetween are joined to each other through dummy joints formed of the same metal as that of the metal joints.

In the humidity sensing apparatus according to the aspect, the two opposite members are fixed to each other through the metal joints and the dummy joints, in which the metal joints join the electrode portions, which transmit electric power or a signal, to each other, and the dummy joints join the dummy electrode portions to each other. Therefore, the two opposite members can be strongly fixed to each other.

In the humidity sensing apparatus according to the aspect, it is preferable that the opposite members are fixed to each other through joining strength between the metal joints and the dummy joints.

In the humidity sensing apparatus according to the aspect, it is not necessary to fill a binder resin into a gap between the two opposite members, and even if the binder resin is filled, the amount thereof is extremely small. Therefore, a junction structure between the two opposite members can be simplified, and the number of steps for joining can be reduced. In addition, the number of obstacles which decrease gas permeability to the gap between the two opposite members is small. Therefore, gas to be measured rapidly reaches from the gap to the humidity sensing portion, and the response of sensing a humidity change can be enhanced.

In the humidity sensing apparatus according to the aspect, it is preferable that the first opposite member is a circuit board; and that the second opposite member is an integrated circuit package.

In the structure, the integrated circuit package, the substrate, and the humidity sensing portion can be disposed to be superimposed on each other. Therefore, a small-sized humidity sensing apparatus can be configured.

In the humidity sensing apparatus according to the aspect, it is preferable that a planar shape of an opposite region where the opposite surface of the first opposite member and the opposite surface of the second opposite member are opposite to each other is rectangular; that the opposite region includes two first edge portions and two second edge portions; that the two first edge portions opposite to each other are positioned at positions at distances from the humidity sensing portion; that the two second edge portions opposite to each other are positioned at positions at shorter distances from the humidity sensing portion than the distances of the first edge portions from the humidity sensing portion; that assemblies of joints including a plurality of metal joints and a plurality of dummy joints are classified into a first group and a second group; that joints of the first group are arranged in a line along the two first edge portions; and that joints of the second group are disposed at positions closer to the humidity sensing portion than the joints of the first group.

Further, in the humidity sensing apparatus according to the aspect, it is preferable that the number of joints constituting the second group is less than the number of joints constituting the first group.

In this case, it is more preferable that the joints of the second group are positioned in a region between the joints of the first group and the humidity sensing portion.

Alternatively, in the humidity sensing apparatus according to the aspect, it is preferable that a planar shape of an opposite region where the opposite surface of the first opposite member and the opposite surface of the second opposite member are opposite to each other is rectangular; that the opposite region includes two first edge portions and two second edge portions; that the two first edge portions opposite to each other are positioned at positions at distances from the humidity sensing portion; that the two second edge portions opposite to each other are positioned at positions at shorter distances from the humidity sensing portion than the distances of the first edge portions from the humidity sensing portion; and that the metal joints and the dummy joints are arranged in a line along the two first edge portions.

In the humidity sensing apparatus according to the aspect, it is preferable that the humidity sensing portion is disposed at a position closer to the edge portions of the opposite members than the center of the opposite surfaces.

By adopting the above-described respective structures, gas to be measured can rapidly reach from the gap to the humidity sensing portion, and the response of sensing a humidity change can be further enhanced.

In the humidity sensing apparatus according to the present invention, the humidity sensing portion is positioned in the gap between the two opposite members. Therefore, since the humidity sensing portion is not exposed to the outside, the humidity sensing portion can be protected. In addition, since the two opposite members are joined to each other through both the metal joints and the dummy joints, the opposite members can be strongly fixed to each other. Since the metal joints and the dummy joints can be formed in the same series of steps, the number of steps for joining the opposite members to each other can also be reduced.

In addition, it is not necessary to fill a fixing resin material into the gap between the two opposite members, and if the resin material is filled, the amount thereof is extremely small. Therefore, gas can be introduced into the humidity sensing portion from the gap, and the response of sensing a humidity change can be enhanced.

BRIEF DESCRIPTION OF THE DRAWINGS

FIG. 5B is a perspective view showing the response to humidity in a second comparative example;

DESCRIPTION OF THE PREFERRED EMBODIMENTS

Figure 1A:
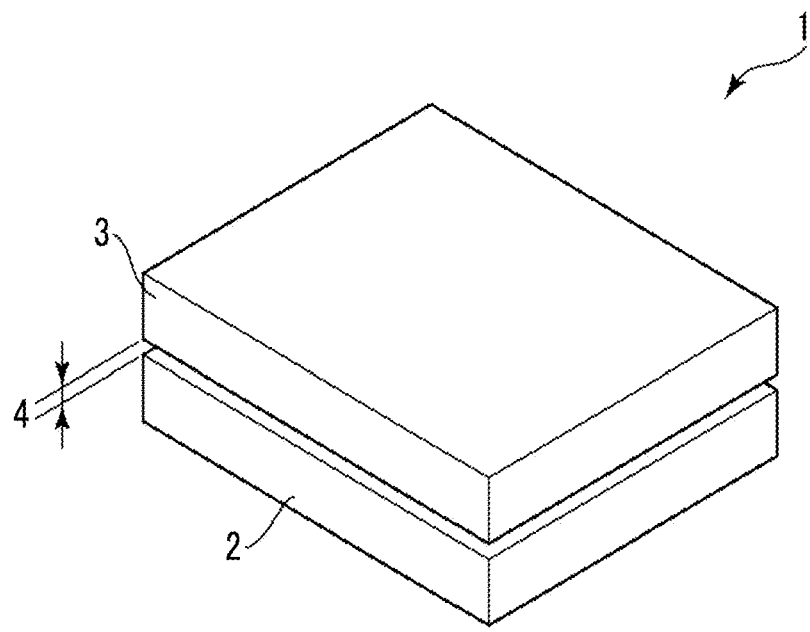
FIG. 1A is a perspective view showing a humidity sensing apparatus according to an embodiment of the present invention.
Figure 1B:
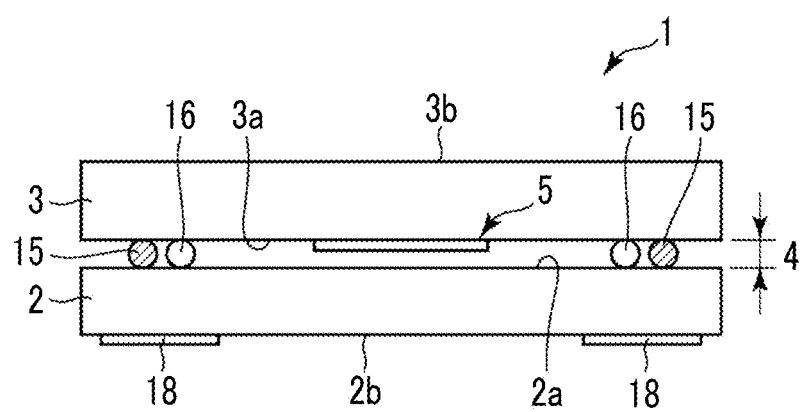
FIG. 1B is a side view showing the humidity sensing apparatus.

A humidity sensing apparatus 1 shown in FIGS. 1A and 1B is configured by superimposing a first opposite member 2 and a second opposite member 3 on each other. The first opposite member 2 is a circuit board including multiple layers, and the second opposite member 3 is an integrated circuit package.

The first opposite member 2 includes an opposite surface 2a and a mounting surface 2b for mounting the first opposite member 2 on a mother board. The second opposite member 3 includes an opposite surface 3a and a top surface 3b. The opposite surface 2a and the opposite surface 3a are planar. The first opposite member 2 and the second opposite member 3 are combined such that the opposite surface 2a and the opposite surface 3a are opposite to each other. As a result, a gap 4 is formed in an opposite region between the opposite surface 2a and the opposite surface 3a.

Figure 2A:
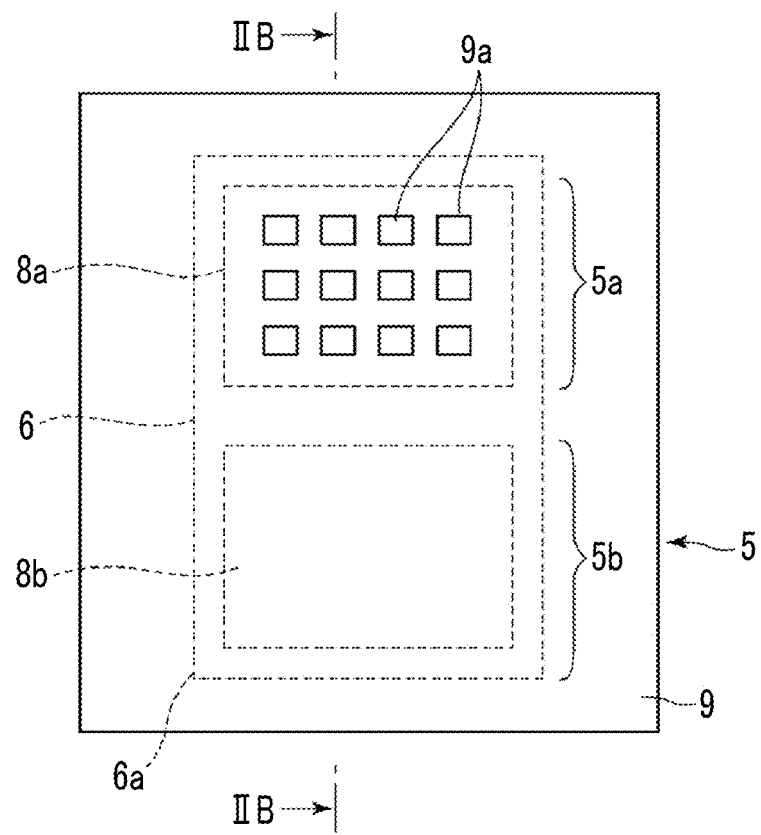
FIG. 2A is an enlarged plan view showing a humidity sensing portion of FIG. 1B when seen from the bottom.
Figure 2B:
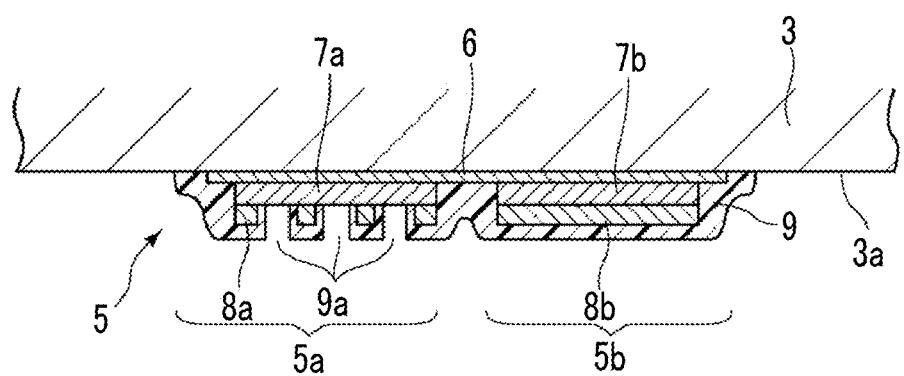
FIG. 2B is a cross-sectional view taken along line IIB-IIB of FIG. 2A.

A humidity sensing portion 5 is mounted on the opposite surface 3a of the second opposite member 3. As shown in FIGS. 2A and 2B, the humidity sensing portion 5 includes a moisture sensitive element 5a and a reference element 5b.

A back-side electrode 6 which functions as a common electrode is provided to the moisture sensitive element 5a and the reference element 5b. In the moisture sensitive element 5a, a moisture sensitive resin layer 7a is superimposed on the back-side electrode 6, and a front-side electrode 8a is superimposed thereon. In the reference element 5b, a moisture sensitive resin layer 7b is superimposed on the back-side electrode 6, and a front-side electrode 8b is superimposed thereon. The moisture sensitive resin layers 7a and 7b are formed of, for example, a polyimide resin material.

The moisture sensitive element 5a and the reference element 5b are coated with a protective resin layer 9. The protective resin layer 9 is formed of a non-hygroscopic inorganic material such as SiN. In the moisture sensitive element 5a, plural openings 9a are formed on the front-side electrode 8a and the protective resin layer 9. Through these openings 9a, the moisture sensitive resin layer 7a in the moisture sensitive element 5a is exposed to the inside of the gap 4 of the opposite region.

The reference element 5b has the same structure as that of the moisture sensitive element 5a. However, since the openings 9a are not formed, the moisture sensitive resin layer 7b is not in contact with external air.

The second opposite member 3 is an integrated circuit package, and the back-side electrode 6 and the front-side electrodes 8a and 8b are connected to an integrated circuit inside the second opposite member 3.

Gas to be measured infiltrates into the gap 4 which is formed in the opposite region between the first opposite member 2 and the second opposite member 3, passes through the plural openings 9a, and comes into contact with the moisture sensitive resin layer 7a inside the moisture sensitive element 5a. The moisture sensitive resin layer 7a has a function of absorbing or releasing moisture depending on the ambient humidity. Therefore, the dielectric constant changes depending on the humidity, and the capacitance between the back-side electrode 6 and the front-side electrode 8a changes depending on the humidity. On the other hand, since the reference element 5b is coated with the non-hygroscopic protective resin layer 9, the capacitance does not change depending on the ambient humidity.

In the integrated circuit, a pulse-like voltage is applied between the front-side electrode 8a of the moisture sensitive element 5a and the back-side electrode 6, and a pulse-like voltage is applied between the front-side electrode 8b of the reference element 5b and the back-side electrode 6. In the moisture sensitive element 5a and the reference element 5b, the sensing output such as a current value changes depending on the capacitance. Therefore, a humidity change can be sensed by obtaining a difference between the sensing output of the moisture sensitive element 5a and the sensing output of the reference element 5b.

Figure 3:
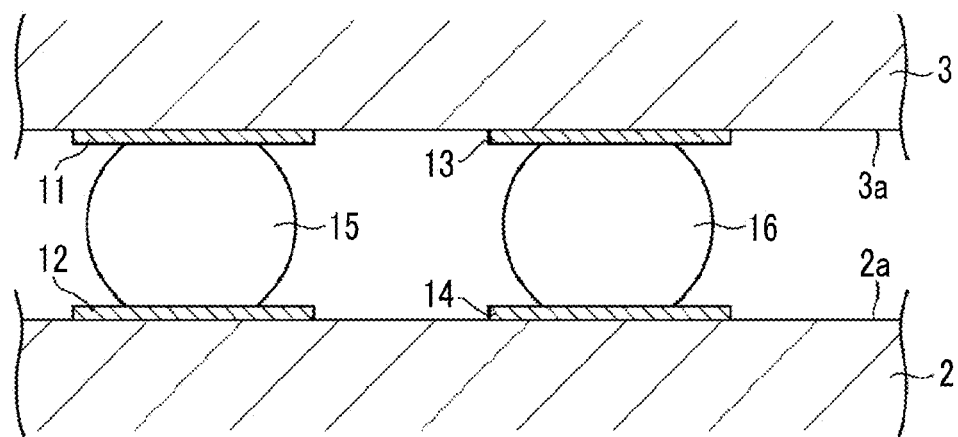
FIG. 3 is a partially enlarged cross-sectional view showing a junction portion of a metal joint and a dummy joint.

As shown in FIG. 3, an electrode portion 11 is formed on the opposite surface 3a of the second opposite member 3, an electrode portion 12 is formed on the opposite surface 2a of the first opposite member 2, and the electrode portion 11 and the electrode portion 12 are opposite to each other with the gap 4 interposed therebetween. The electrode portion 11 and the electrode portion 12 are joined to each other through a metal joint 15.

The electrode portion 12 formed on the opposite surface 2a of the first opposite member 2, which is the multilayer substrate, is obtained by plating a surface of a copper electrode pad with gold. The electrode portion 11 formed on the opposite surface 3a of the second opposite member 3, which is the integrated circuit package, is a gold-plated metal pad. The metal joint 15 is a gold ball and is supplied between the electrode portion 11 and the electrode portion 12. This metal joint 15 is applied with ultrasonic vibration and joins the electrode portions 11 and 12 to each other through diffused junction.

Alternatively, a metal bump having at least a surface formed of gold may be formed on one of the electrode portions 11 and 12 as a metal joint instead of using the gold ball, and this metal bump may be joined to another electrode portion through eutectic bonding or diffused junction.

As shown in FIG. 1B, plural terminal portions 18 are formed on the mounting surface 2b of the first opposite member 2 which is the multilayer substrate, and each of the terminal portions 18 is electrically connected to the electrode portion 12. The electrode portion 11 provided on the second opposite member 3 which is the integrated circuit package is connected to the integrated circuit. A capacitance change of the humidity sensing portion 5 is sensed in the integrated circuit, a sensing signal representing the humidity change is generated, and this sensing signal is transmitted from the electrode portion 11 to the electrode portion 12 through the metal joint 15 and is further transmitted from the terminal portion 18 to the mother board. In addition, an electric power supplied from the mother board is transmitted from the terminal portion 18 to the electrode portion 12 and is further transmitted from the metal joint 15 to the integrated circuit through the electrode portion 11.

As shown in FIG. 3, a dummy electrode portion 13 is provided on the opposite surface 3a of the second opposite member 3, and a dummy electrode portion 14 is provided on the opposite surface 2a of the first opposite member 2. The dummy electrode portion 13 and the dummy electrode portion 14 opposite to each other are joined through a dummy joint 16.

The dummy electrode portion 13 provided on the opposite surface 3a of the second opposite member 3 is formed of the same material in the same structure as those of the electrode portion 11. The dummy electrode portion 14 provided on the opposite surface 2a of the first opposite member 2 is formed of the same material in the same structure as those of the electrode portion 12. The dummy joint 16 is formed of the same material in the same structure as those of the metal joint 15.

The dummy electrode portion 13 provided on the second opposite member 3 is not connected to the internal integrated circuit, and the dummy electrode portion 14 provided on the first opposite member 2 is not electrically connected to the terminal portion 18. In addition, even when the dummy electrode portion 13 is connected to the integrated circuit and the dummy electrode portion 14 is electrically connected to the terminal portion 18, the dummy electrode portions 13 and 14 are not supplied with electric power or a signal and are not used for electric conduction.

Figure 4A:
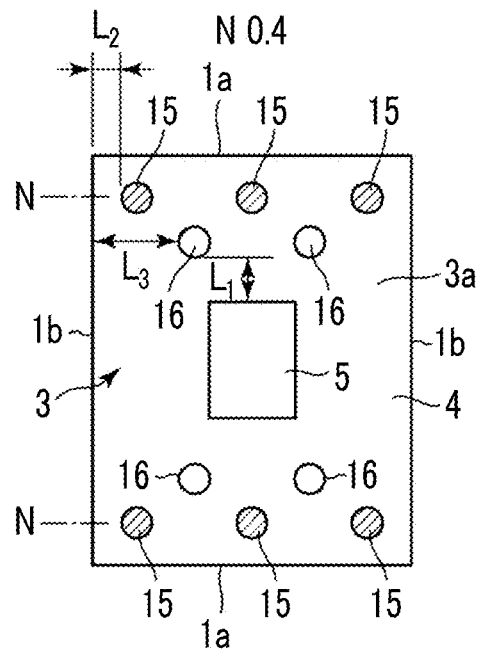
FIGS. 4A, 4B, and 4C are plan views showing the arrangements of metal joints and dummy joints in the respective embodiments.
Figure 4B:
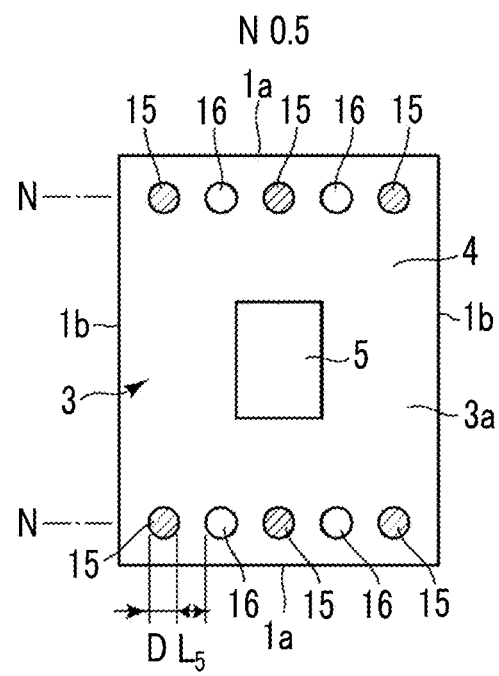
Figure 4C:
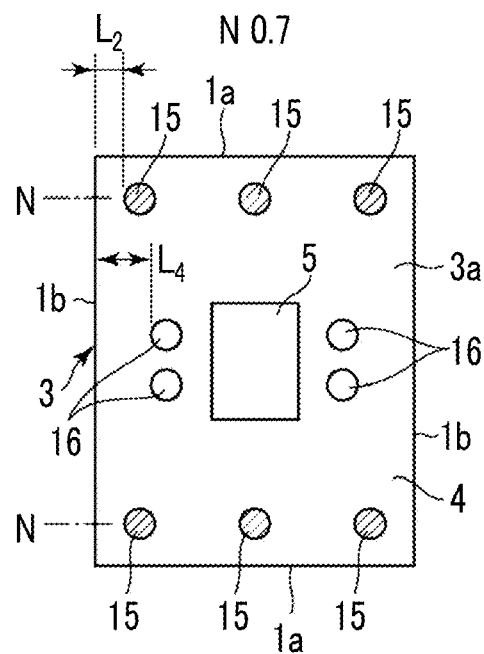

FIGS. 4A to 4C are bottom views showing the second opposite member 3 when seen from the opposite surface 3a side. As shown in FIGS. 1B and 4A to 4C, plural metal joints 15 and plural dummy joints 16 are disposed in the gap 4 which is formed in the opposite region between the first opposite member 2 and the second opposite member 3. In FIGS. 1B and 4A to 4C, only the metal joints 15 are hatched in order to distinguish the metal joints 15 and the dummy joints 16 from each other.

In the humidity sensing apparatus 1 according to embodiments shown in FIGS. 4A, 4B, and 4C, six metal joints 15 and four dummy joints 16 are provided.

In the second opposite member 3 accommodating the integrated circuit, the number of metal joint 15 is set as required in the specification. Since the dummy joints 16 reinforce the joining strength between the two opposite members 2 and 3, the number thereof is determined depending on the sizes and the like of the first opposite member 2 and the second opposite member 3. However, in order not to decrease gas permeability to the inside of the gap 4 between the two opposite members 2 and 3, it is preferable that the number of dummy joints 16 may be equal to or less than the number of metal joints 15.

In the humidity sensing apparatus 1, the first opposite member 2 and the second opposite member 3 are fixed to each other through the joining strength of the metal joints 15 and the joining strength of the dummy joints 16. The metal joints 15 and the dummy joints 16 are formed of the same metal material, and the junction structure of the metal joints 15 and the junction structure of the dummy joints 16 can be formed through a series of operations in the same step. Accordingly, the first opposite member 2 and the second opposite member 3 can be strongly fixed to each other through a small number of steps.

In the gap 4 between the first opposite member 2 and the second opposite member 3, only the metal joints 15 and the dummy joints 16 having a spherical shape or a columnar shape are present. Therefore, the gas permeability of the gap 4 is improved, and thus gas to be measured can rapidly reach the humidity sensing portion 5 after infiltrating into the gap 4 and passing through gaps between the metal joints 15 and the dummy joints 16. Accordingly, the response of the humidity sensing portion 5 sensing a humidity change of gas can be enhanced.

The first opposite member 2 and the second opposite member 3 are fixed to each other through the joining strengths of the metal joints 15 and the dummy joints 16. Therefore, it is not necessary to fill a reinforcing resin such as an underfill into the gap 4, and thus the assembly work is easy. In the present invention, it is preferable that no reinforcing resin is present in the gap 4. However, a small amount of reinforcing resin may be filled into the gap 4 as auxiliary means in a state where the joining strength of the two opposite members 2 and 3 are secured mainly through the joining strengths of the metal joints 15 and the dummy joints 16.

FIGS. 4A, 4B, and 4C show preferable examples of the arrangement structure of the metal joints 15 and the dummy joints 16.

FIGS. 4A, 4B, and 4C are bottom views showing the opposite member 3 when seen from the opposite surface 3a side. In the embodiments, since the opposite member 2 and the opposite member 3 have the same shape and the same dimension, the planar shape of the gap 4 formed between the two opposite members 2 and 3, that is, the planar shape of the opposite region where the opposite surface 2a and the opposite surface 3a are opposite to each other is the same as that of the opposite surface 2a.

In FIGS. 4A to 4C, the planar shape of the opposite region where the opposite surface 2a and the opposite surface 3a are opposite to each other, that is, the planar shape of the gap 4 is rectangular, and the planar shape of the opposite region (the planar shape of the gap 4) includes two first edge portions 1a and 1a and two second edge portions 1b and 1b. The first edge portions 1a and 1a are at distances from the center of the humidity sensing portion 5, and the second edge portions 1b and 1b are at shorter distances from the center of the humidity sensing portion 5 than the distances of the first edge portions 1a and 1a from the center of the humidity sensing portion 5. The first edge portions 1a and 1a corresponds to short sides of the rectangle, and the second edge portions 1b and 1b corresponds to long sides of the rectangle.

When the shape of the opposite surface 2a of the opposite member 2 is different from that of the opposite surface 3a of the opposite member 3, the planar shape of the opposite region, that is, the planar shape of the gap 4 is the planar shape of a region where the two opposite surfaces 2a and 3a are superimposed on each other. Accordingly, among edge portions of the short sides of the first opposite member 2 and edge portions of the short sides of the second opposite member 3, the first edge portions 1a and 1a shown in FIGS. 4A to 4C are edge portions of the short sides closer to the center of the humidity sensing portion 5 (or the center of the entire humidity sensing apparatus 1). Among edge portions of the long sides of the first opposite member 2 and edge portions of the long sides of the second opposite member 3, the second edge portions 1b and 1b are edge portions of the long sides closer to the center of the humidity sensing portion 5 (or the center of the entire humidity sensing apparatus 1). According to this definition, the rectangle shown in FIGS. 4A to 4C represents the planar shape of the opposite region or the planar shape of the gap 4.

In an example shown in FIG. 4A, three metal joints 15 are arranged along a line N parallel to the two first edge portions 1a and 1a. The number of dummy joints 16 is less than the number of metal joints 15. The dummy joints 16 are positioned at positions at a distance L1 from the humidity sensing portion 5 to the first edge portions 1a. That is, the dummy joints 16 are disposed in a belt-shaped region between the humidity sensing portion 5 and the metal joints 15. A distance L3 between the dummy joint 16 and the second edge portion 1b is set to be longer than a distance L2 between the second edge portion 1b and the metal joint 15.

In an example shown in FIG. 4C, as in the example of FIG. 4A, three metal joints 15 are arranged along line N parallel to the two first edge portions 1a and 1a. The dummy joints 16 are disposed between the second edge portions 1b and the humidity sensing portion 5. A distance L4 between the dummy joint 16 and the second edge portion 1b is set to be longer than the distance L2 between the second edge portion 1b and the metal joint 15.

In an example shown in FIG. 4B, three metal joints 15 and two dummy joints 16 are arranged in a line along the line N parallel to the first edge portions 1a and 1a. In this example, an obstacle is not present and a large space is formed between the two second edge portions 1b and 1b and the humidity sensing portion 5.

When the joints 15 and 16 are closest to each other as shown in FIG. 4B, it is preferable that a distance L5 is longer than a diameter D of the joints 15 and 16. With such a configuration, gas to be measured can pass through a gap between the adjacent joints 15 and 16.

In the example shown in FIG. 4B, a large space is formed between the humidity sensing portion 5 and the second edge portions 1b and 1b which are at the short distances from the center of the humidity sensing portion 5 (or the center of the entire humidity sensing apparatus 1). Therefore, gas to be measured infiltrates into the gap 4 from the second edge portions 1b and 1b and easily comes into contact with the humidity sensing portion 5. Further, gas can be introduced into the humidity sensing apparatus 1 from gaps between the joints 15 and 16 arranged along the first edge portion 1a. Therefore, a humidity change in the outside of the humidity sensing apparatus 1 can be rapidly sensed by the humidity sensing portion 5, and the sensing response to the humidity change is improved.

In the example shown in FIG. 4A, the dummy joints 16 are provided in a region between the humidity sensing portion 5 and the metal joints 15 and are more distant from the second edge portion 1b than the metal joints 15. Accordingly, gas can be easily introduced into the humidity sensing portion 5 not only from the second edge portion 1b but also from the first edge portion 1a. Therefore, a humidity change in the outside of the humidity sensing apparatus 1 can be rapidly sensed by the humidity sensing portion 5, and the sensing response to the humidity change is improved.

In the example shown in FIG. 4C, the dummy joints 16 are provided in a region between the humidity sensing portion 5 and the second edge portions and are more distant from the second edge portion 1b than the metal joints 15. Therefore, an opening of the second edge portion 1b is formed to be large, and gs can be rapidly introduced into the humidity sensing portion 5 from the second edge portion 1b. Even with this structure, a humidity change in the outside of the humidity sensing apparatus 1 can be rapidly sensed by the humidity sensing portion 5, and the sensing response to the humidity change is improved.

In FIGS. 4A, 4B, and 4C, the metal joints 15 are arranged along the line N, and the dummy joints 16 are arranged at positions other than the positions of the metal joints 15. However, in these examples, even if the positions of the metal joints 15 and the dummy joints 16 are exchanged, the condition of the sensing response to the humidity change is not changed as long as the arrangement of the joints 15 and 16 is not changed.

In the present invention, as shown in FIGS. 4A, 4B, and 4C, it is preferable that the joints 15 and 16 are arranged in a line along the first edge portions 1a and 1a which are at long distances from the center of the humidity sensing portion 5; and that a less number of joints 15 and 16 than that of joints forming a line are disposed at positions closer to the center than the line.

In FIGS. 5A to 10, simulation results of comparative examples and embodiments are compared to each other. In this simulation, a relationship between the arrangement of the joints 15 and 16 and the response to the humidity change of the center of the gap 4 is investigated.

In FIGS. 5A to 10, simulation data are represented by No. 1 to No. 7. No. 1 and No. 2 are comparative examples, and No. 3 to No. 7 are embodiments according to the present invention. The preferable example of FIG. 4A corresponds No. 4 of FIG. 7, the preferable example of FIG. 4B corresponds to No. 5 of FIG. 8, and the preferable example of FIG. 4C corresponds to No. 7 of FIG. 10.

In all the simulation data No. 1 to No. 7, the length of the first edge portion 1a of the rectangle, which is the opposite region between the opposite surface 2a and the opposite surface 3a, is 0.84 mm, the length of the second edge portion 1b of the rectangle is 1.14 mm, and the thickness of the gap 4, that is, the distance between the first opposite member 2 and the second opposite member 3 opposite to each other is 0.06 mm.

The simulation results of FIGS. 5A to 10 represent a humidity change in a gas layer (air layer) present in the gap 4. Therefore, in No. 2 to No. 7, portions where the metal joints 15 and the dummy joints 16 are present are expressed by round holes. The diameter of the round holes is the diameter of the metal joints 15 and the dummy joints 16 and is set to be 0.08 mm.

In FIGS. 5A to 10, a relative humidity in each portion of a gas layer (air layer) after 1 msec from an instantaneous increase from 0% to 100% in the relative humidity of the outside of the humidity sensing apparatus 1 is represented in monochrome gravitation. The deeper the black color of a portion, the higher the humidity.

Figure 5A:
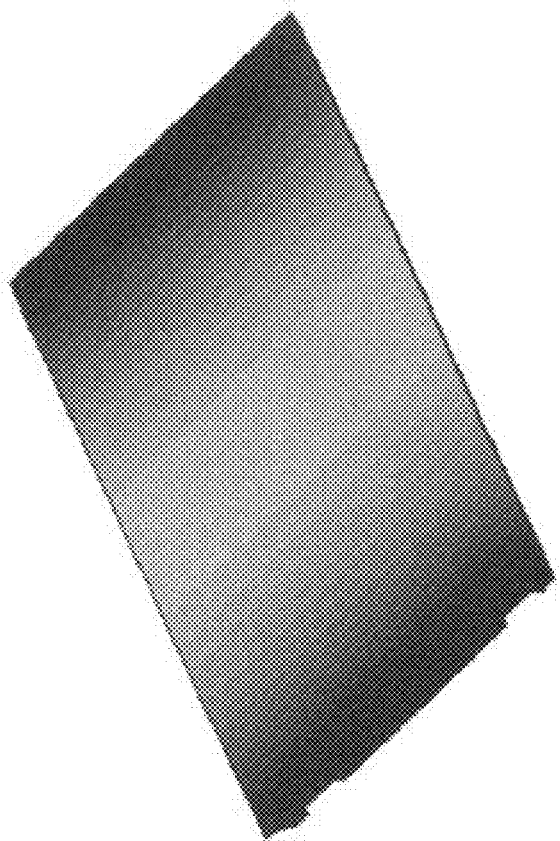
FIG. 5A is a perspective view showing the response to humidity in a first comparative example.
Figure 5A:
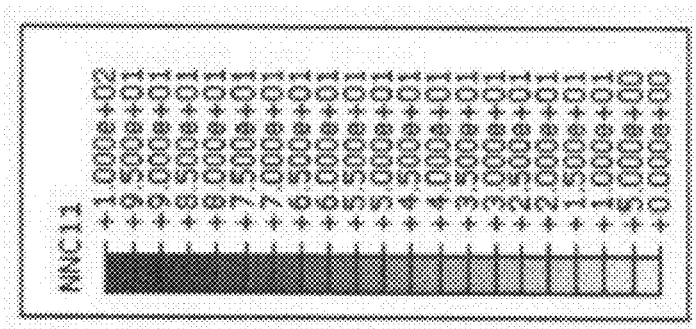

In No. 1 of FIG. 5A which is a first comparative example, the second edge portions 1b and 1b as the long sides are closed over the entire length, and the first edge portions 1a and 1a as the short sides are open. The second edge portions 1b and 1b which are at short distances from the center of the humidity sensing apparatus 1 are closed, and the first edge portions 1a and 1a which are at long distances from the center of the humidity sensing apparatus 1 are open. Therefore, the humidity of a wide region of the center is not substantially increased even after 1 msec.

In No. 2 shown in FIG. 5B which is a second comparative example, it is assumed that three metal joints 15 are arranged in a line along the line N shown in FIGS. 4A to 4C, and the dummy joint 16 are not used. In this comparative example, the second edge portion 1b which is at a short distance from the center open over then entire length. Therefore, after 1 msec, the humidity of the center is increased uniformly in all the directions.

In the embodiments of FIGS. 6 to 10, the humidity change is rapidly transferred to the center as compared to the first comparative example of No. 1. In particular, in No. 4, No. 5, and No. 7 described as the preferable examples in FIGS. 4A, 4B, and 4C, the transferred state of the humidity change to the center is similar to that of the second comparative example shown in FIG. 5B.

Figure 11:
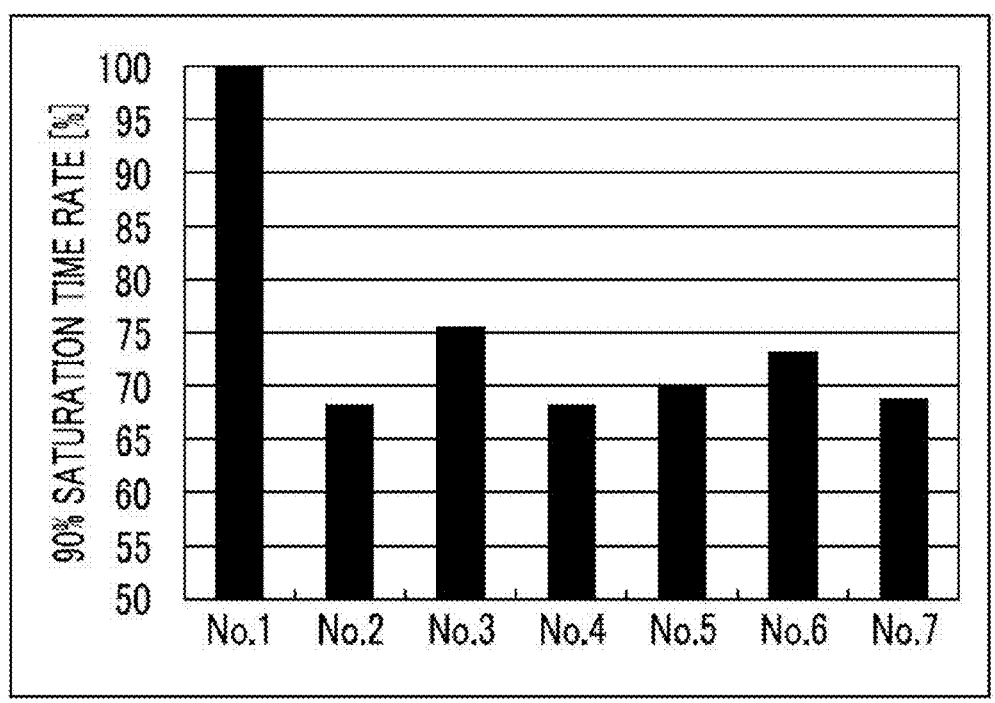
FIG. 11 is a line graph for comparing the responses to humidity in the respective comparative examples and the respective embodiments.

FIG. 11 shows the results of a simulation where the time periods required for the relative humidity of the center of the gap 4 to reach 90% are compared to each other when the relatively humidity of gas (air) outside of the humidity sensing apparatus 1 is instantaneously increased from 0% to 100%. When the time period required for the relative humidity to reach 90% in the comparative example of No. 1 is represented by 100%, the time periods required for the relative humidity to reach 90% in the respective data of No. 2 to No. 7 are represented in percentage relative to No. 1.

According to the simulation results of FIG. 11, in No. 3 to No. 7 according to the embodiments of the invention, the humidity of the center is rapidly increased as compared to the comparative example of No. 1. Among these, in No. 4, No. 5, and No. 7 shown in FIGS. 4A, 4B, and 4C, the humidity increase rate of the center is equal to that of the comparative example of No. 2.

Figure 6:
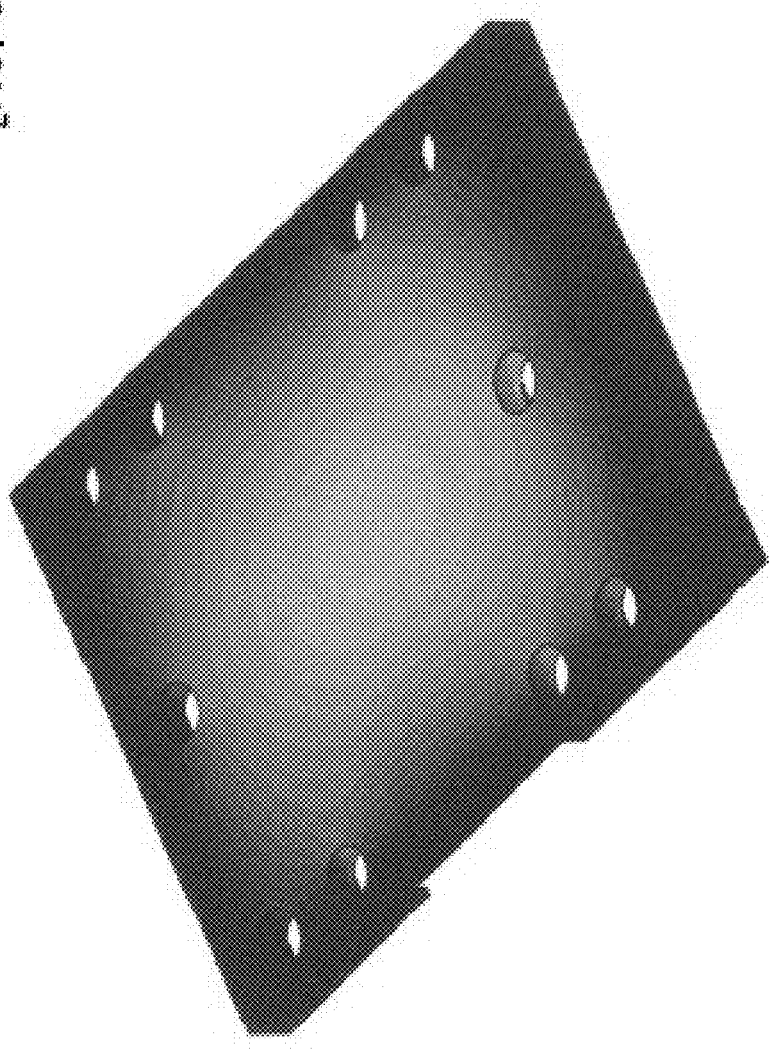
FIG. 6 is a perspective view showing the response to humidity in a first embodiment.
Figure 6:
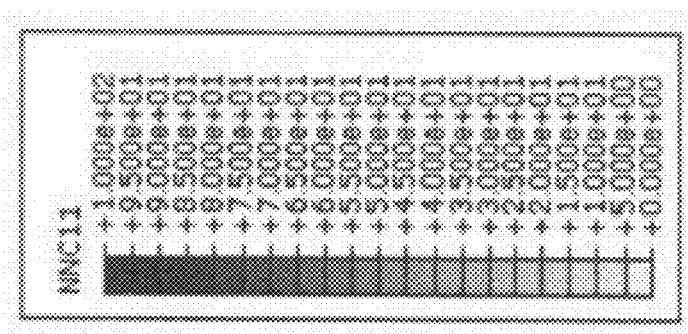
Figure 7:
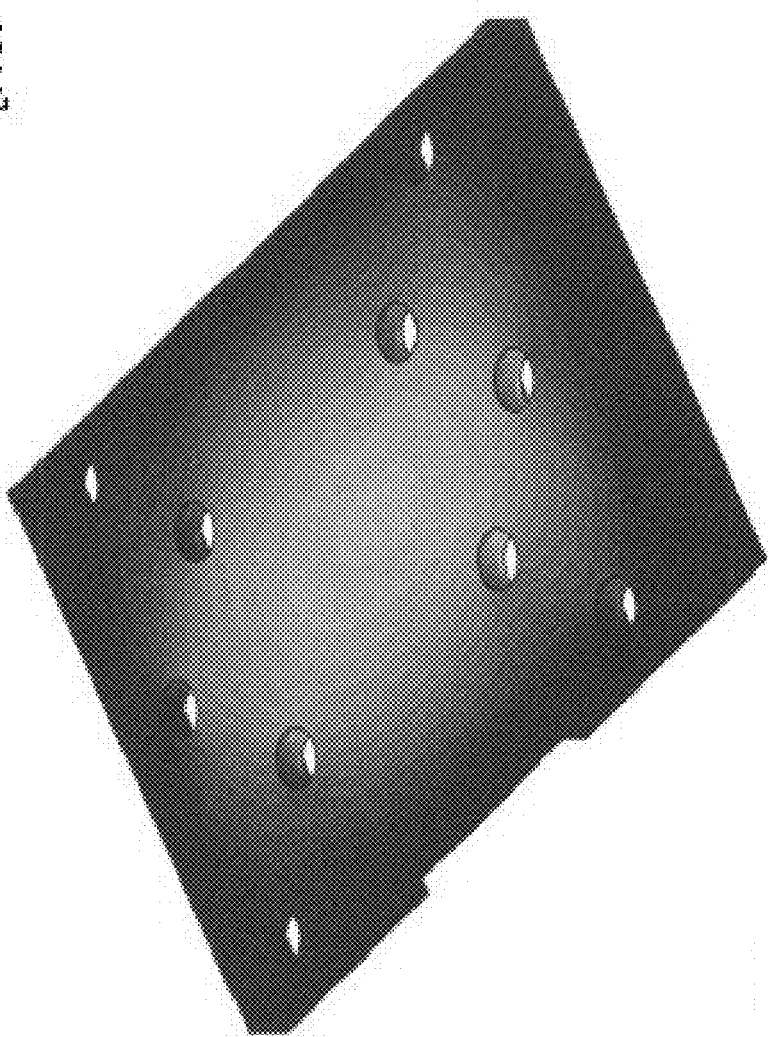
FIG. 7 is a perspective view showing the response to humidity in a second embodiment.
Figure 7:
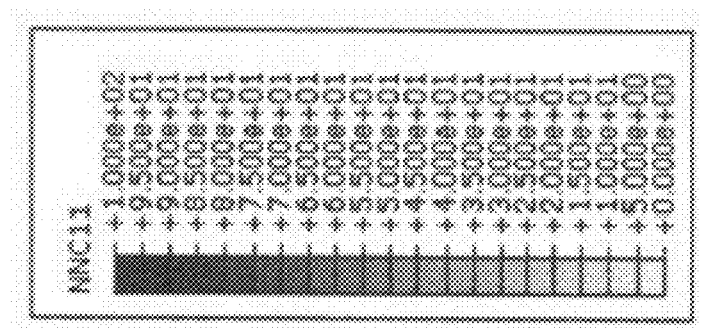
Figure 8:
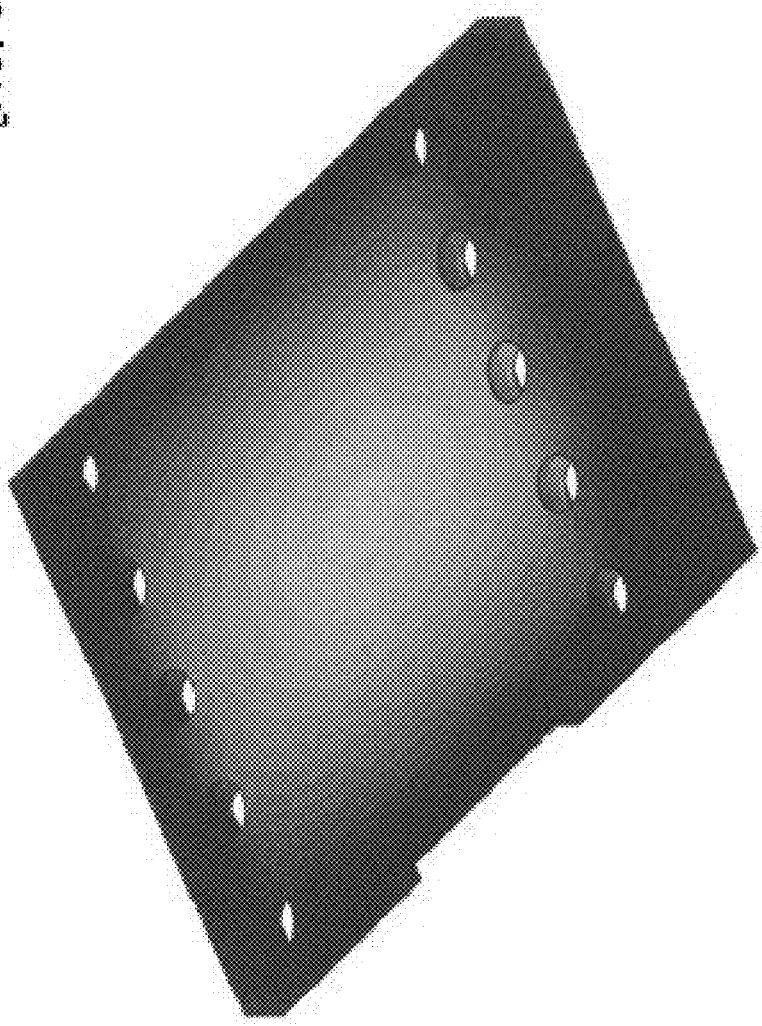
FIG. 8 is a perspective view showing the response to humidity in a third embodiment.
Figure 8:
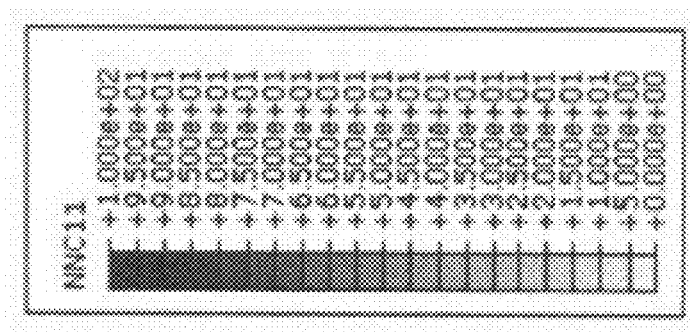
Figure 9:
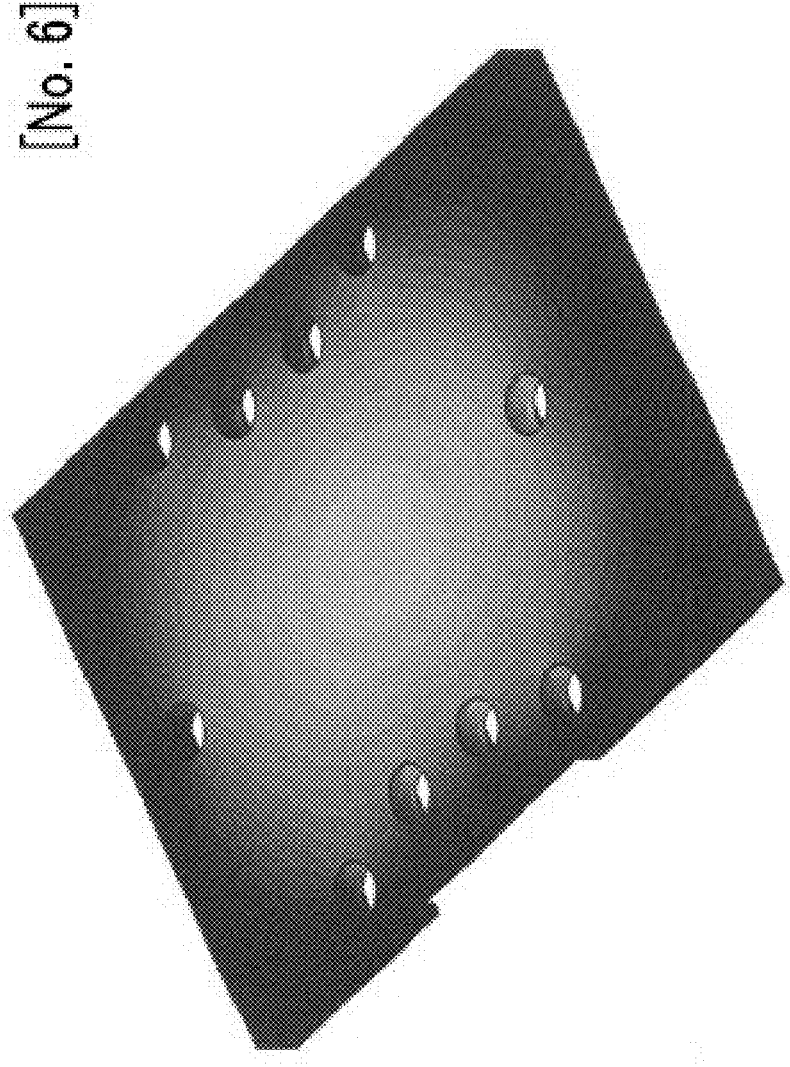
FIG. 9 is a perspective view showing the response to humidity in a fourth embodiment.
Figure 9:
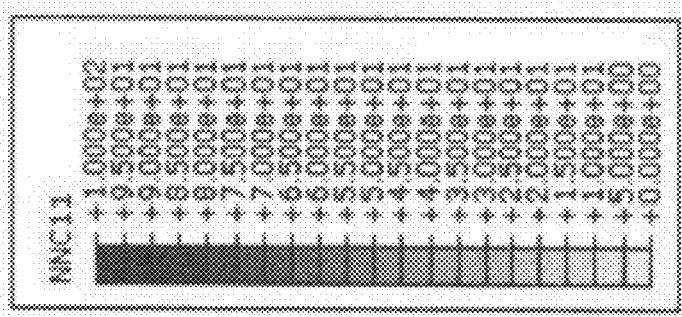
Figure 10:
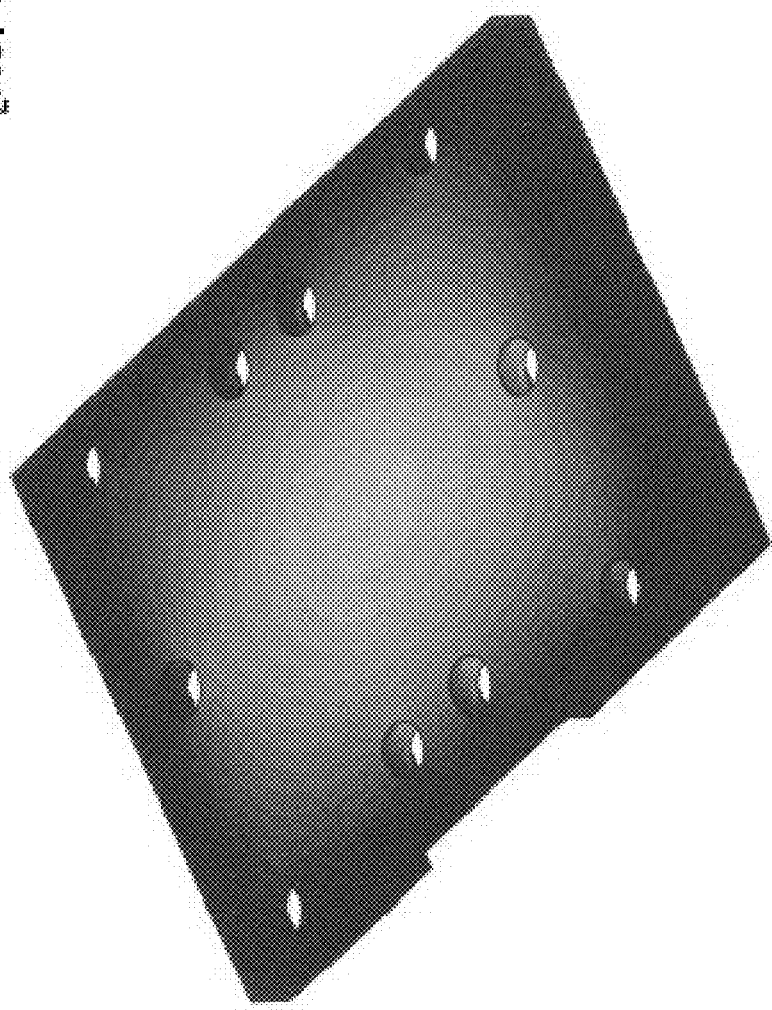
FIG. 10 is a perspective view showing the response to humidity in a fifth embodiment.
Figure 10:
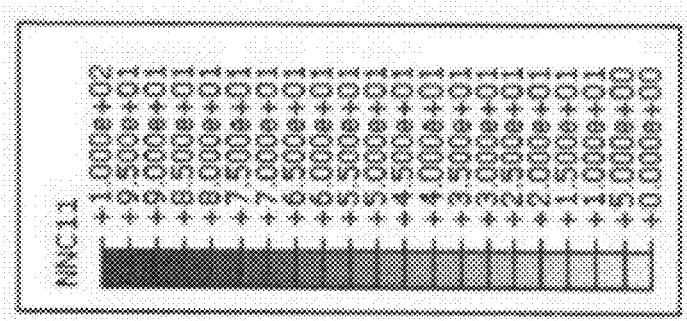

In No. 3 shown in FIG. 6, four joints 15 and 16 are present along the second edge portions 1b and 1b which are at short distances from the center. Therefore, the transfer of water vapor from the second edge portions 1b and 1b to the center tends to be slightly delayed. In the data of No. 6, unlike No. 7, the joints 15 and 16 which should be arranged along the line N are positioned at positions that block the second edge portions 1b and 1b. Therefore, the transfer of water vapor from the second edge portions 1b and 1b to the center tends to be slightly delayed.

It can be understood from the above results that, in the embodiments shown in No. 4, No. 5, and No. 7, the humidity of the center can be rapidly changed as in the case of the second comparative example where only the metal joints 15 are used, and the humidity sensing apparatus 1 having superior response can be configured.

Figure 12A:
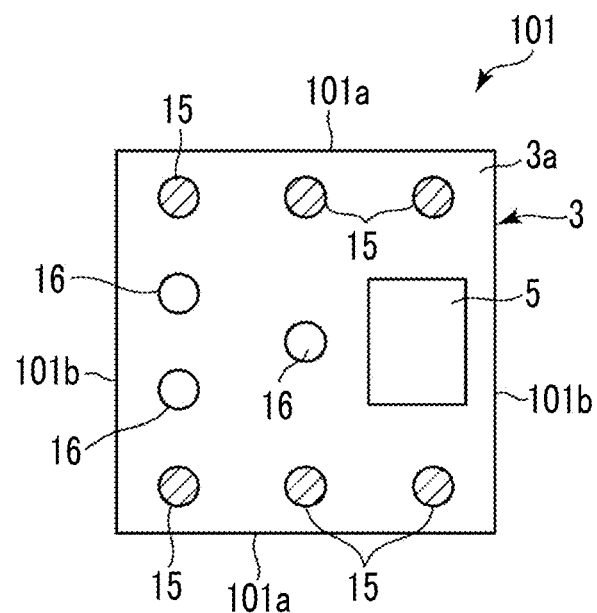
FIGS. 12A and 12B are diagrams showing the arrangement position of a humidity sensing portion of a humidity sensing apparatus according to still another embodiment.
Figure 12B:
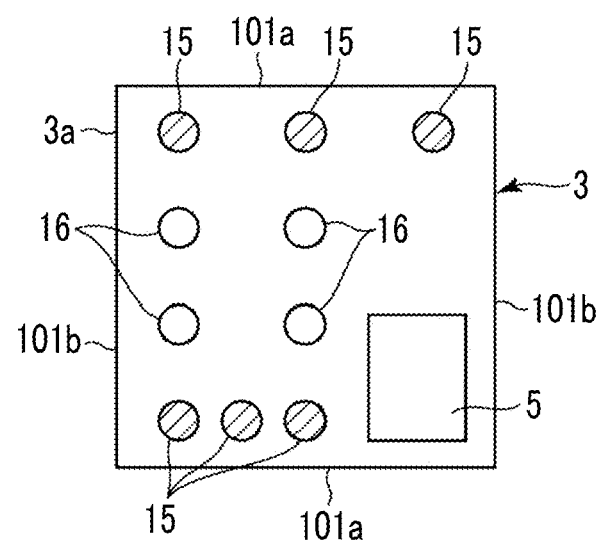

In a humidity sensing apparatus 101 according to still another embodiment shown in FIGS. 12A and 12B, first edge portion 101a and 101a match with second edge portions 101b and 101b, and the planar shape of the gap 4 between the first opposite member 2 and the second opposite member 3 (the planar shape of the gap 4) is square.

The humidity sensing portion 5 is positioned not at the center of the square but at a position close to at least one of the first edge portion 101a and the second edge portion 101b.

In this embodiment, the humidity sensing portion 5 is connected to the outside of the gap 4 with a short distance. Therefore, when the humidity changes, the response characteristics of the sensing output are superior.

In the above-described embodiments, the first opposite member 2 is the multilayer substrate, and the second opposite member 3 is the integrated circuit package. However, the second opposite member 3 on which the humidity sensing portion 5 is mounted may be the multilayer substrate, and the first opposite member 2 may be the integrated circuit package. In addition, both the first opposite member 2 and the second opposite member 3 may be the multilayer substrate.

In addition, the structure of the moisture sensitive element 5a and the reference element 5b is not limited to the structure shown in FIG. 2. For example, comb-like electrodes may be opposite to each other on a plane such that a change in the capacitance between the electrodes is sensed.

It should be understood by those skilled in the art that various modifications, combinations, sub-combinations and alterations may occur depending on design requirements and other factors insofar as they are within the scope of the appended claims of the equivalents thereof.

What is claimed is:

1. A humidity sensing apparatus comprising:
   a first member having a first surface;
   a second member opposing the first member, the second member having a second surface opposing the first surface of the first member with a gap provided therebetween;
   a humidity sensing portion provided on the second surface of the second member;
   a plurality of electrode portions and a plurality of dummy electrode portions provided on each of the first and second surfaces, such that the electrode portions on the first surface and the electrode portions on the second surface oppose each other, and the dummy electrode portions on the first surface and the dummy electrode portions on the second surface oppose each other;
   a plurality of conductive metal joints joining the electrode portions on the first surface and the electrode portions on the second surface opposing each other; and
   a plurality of dummy joints joining the dummy electrode portions on the first surface and the dummy electrode portions on the second surface opposing each other, thereby reinforcing a joining strength between the first and second members, the dummy joints being formed of a same metal as that of the metal joint,
   wherein the dummy electrode portions and dummy joints are configured not to receive electric power or signals and do not contribute electric conduction in the humidity sensing apparatus,
   wherein an opposing area in which the first and second surfaces oppose each other has a rectangular shape in a plan view, the opposing area having a pair of first edges and a pair of second edges, the first edges being positioned at first distances from the humidity sensing portion, and the second edges being at second distances from the humidity sensing portion shorter than the first distances,
   and wherein the plurality of metal joints and the plurality of dummy joints are divided into a first group and a second group of joints, the joints in the first group being arranged in a line along the first edges so as to have a third distance from the humidity sensing portion, and the joints in the second group are arranged in a line along the second edges so as to have a fourth distance from the humidity sensing portion smaller than the third distance, thereby enhancing a responsiveness of the humidity sensing apparatus.

2. The humidity sensing apparatus according to claim 1, wherein the first and second members are fixed to each other through joining force of the metal joints and the dummy joints.

3. The humidity sensing apparatus according to claim 1, wherein
   the first member is a circuit board, and
   the second member is an integrated circuit package.

4. The humidity sensing apparatus according to claim 1, wherein a number of joints constituting the second group is less than a number of joints constituting the first group.

5. The humidity sensing apparatus according to claim 1, wherein the joints in the second group are positioned in a region between the joints in the first group and the humidity sensing portion.

6. A humidity sensing apparatus comprising:
   a first member having a first surface;
   a second member opposing the first member, the second member having a second surface opposing the first surface of the first member with a gap provided therebetween;
   a humidity sensing portion provided on the second surface of the second member;
   a plurality of electrode portions and a plurality of dummy electrode portions provided on each of the first and second surfaces, such that the electrode portions on the first surface and the electrode portions on the second surface oppose each other, and the dummy electrode portions on the first surface and the dummy electrode portions on the second surface oppose each other;
   a plurality of conductive metal joints joining the electrode portions on the first surface and the electrode portions on the second surface opposing each other; and
   a plurality of dummy joints joining the dummy electrode portions on the first surface and the dummy electrode portions on the second surface opposing each other, thereby reinforcing a joining strength between the first and second members, the dummy joints being formed of a same metal as that of the metal joint,
   wherein the dummy electrode portions and dummy joints are configured not to receive electric power or signals and do not contribute electric conduction in the humidity sensing apparatus,
   wherein an opposing area in which the first and second surfaces oppose each other has a rectangular shape in a plan view, the opposing area having a pair of first edges and a pair of second edges, the first edges being positioned at first distances from the humidity sensing portion, and the second edges being at second distances from the humidity sensing portion shorter than the first distances,
   and wherein the metal joints and the dummy joints are arranged in a line only along the first edges, thereby enhancing a responsiveness of the humidity sensing apparatus.

7. A humidity sensing apparatus comprising:
   a first member having a first surface;
   a second member opposing the first member, the second member having a second surface opposing the first surface of the first member with a gap provided therebetween;
   a humidity sensing portion provided on the second surface of the second member;
   a plurality of electrode portions and a plurality of dummy electrode portions provided on each of the first and second surfaces, such that the electrode portions on the first surface and the electrode portions on the second surface oppose each other, and the dummy electrode portions on the first surface and the dummy electrode portions on the second surface oppose each other;
   a plurality of conductive metal joints joining the electrode portions on the first surface and the electrode portions on the second surface opposing each other; and a plurality of dummy joints joining the dummy electrode portions on the first surface and the dummy electrode portions on the second surface opposing each other, thereby reinforcing a joining strength between the first and second members, the dummy joints being formed of a same metal as that of the metal joint, wherein the dummy electrode portions and dummy joints are configured not to receive electric power or signals and do not contribute electric conduction in the humidity sensing apparatus, and wherein the humidity sensing portion is disposed at a position closer to at least one of the first and second edges off the center of the opposing area, thereby enhancing a responsiveness of the humidity sensing apparatus.

8. The humidity sensing apparatus according to claim 7, wherein none of the conductive metal joints and the dummy joints are formed between the humidity sensing portion and the at least one of the first and second edges closer to which the humidity sensing portion is disposed.

* * * * *